United States Patent [19]

Teele

[11] Patent Number: 4,601,295
[45] Date of Patent: * Jul. 22, 1986

[54] EAR PATHOLOGY DIAGNOSIS APPARATUS AND METHOD

[76] Inventor: John H. Teele, 22 Ruthellen Rd., Chelmsford, Mass. 01824

[*] Notice: The portion of the term of this patent subsequent to Jul. 17, 2001 has been disclaimed.

[21] Appl. No.: 557,123
[22] PCT Filed: Mar. 16, 1983
[86] PCT No.: PCT/US83/00380
§ 371 Date: Nov. 15, 1983
§ 102(e) Date: Nov. 15, 1983
[87] PCT Pub. No.: WO83/03192
PCT Pub. Date: Sep. 29, 1983

Related U.S. Application Data

[63] Continuation-in-part of Ser. No. 358,831, Mar. 16, 1982, Pat. No. 4,459,966.

[51] Int. Cl.$^4$ .............................................. A61B 5/12
[52] U.S. Cl. .................................... 128/746; 73/585; 73/587; 73/589
[58] Field of Search ............... 128/642, 151, 784, 789, 128/746; 73/585, 587, 589

[56] References Cited

U.S. PATENT DOCUMENTS

| 3,294,193 | 12/1966 | Zwislocki | 128/746 X |
| 3,395,697 | 8/1968 | Mendelson | 128/746 |
| 3,757,769 | 9/1973 | Arguimbau et al. | 128/746 |
| 3,882,848 | 5/1975 | Klar et al. | 128/746 |
| 3,949,735 | 4/1976 | Klar et al. | 73/585 X |
| 4,002,161 | 1/1977 | Klar et al. | 128/746 |
| 4,009,707 | 3/1977 | Ward | 128/746 |
| 4,057,051 | 11/1977 | Kerovac | 73/573 X |
| 4,079,198 | 3/1978 | Bennett | 128/746 |
| 4,122,841 | 10/1978 | Rock et al. | 128/746 |
| 4,201,225 | 5/1980 | Bethea, III et al. | 128/746 |
| 4,237,905 | 12/1980 | Keller et al. | 128/746 |
| 4,289,143 | 9/1981 | Canavesio et al. | 73/589 X |
| 4,459,996 | 7/1984 | Teele . | |

FOREIGN PATENT DOCUMENTS 0147313 4/1981 Fed. Rep. of Germany ...... 128/746

OTHER PUBLICATIONS

Buczko; "Principal Respects of Development of Acoustic Impedance Meter"; *Medicor News*, (Hungary), No. 1, 1978, pp. 39-45.
Modena et al.; "A New Artifical Ear for Telephone Use"; *J. Acoustic Soc. Am.*, 63(5), 5-178, pp. 1604-1610.

Primary Examiner—Andrew H. Metz
Assistant Examiner—Anthony McFarlane
Attorney, Agent, or Firm—Cesari and McKenna

[57] ABSTRACT

A method and apparatus for diagnosing pathologies of the ear, particularly pathologies such as otitis media, directs into the ear canal a sequence of acoustic waves covering a range of frequencies from a few hundred Hz to several kHz and determines the presence or absence of resonance when the incident and reflected waves are combined. The measurements are made without pressurizing the ear canal and it is not required that the contact between the instrument and the ear be air-tight. Accordingly, essentially no discomforture of the patient results from use of the instrument. The requisite measurements are made quickly (of the order of tens of milliseconds) and thus the distorting effects of patient movement are effectively eliminated. An improved version of the instrument is completely self-contained and hand-held and has the form of a "tee" in which the resonant frequency and amplitude are visually indicated by means of horizontally-and-vertically disposed arrays of light-emitting diodes.

7 Claims, 10 Drawing Figures

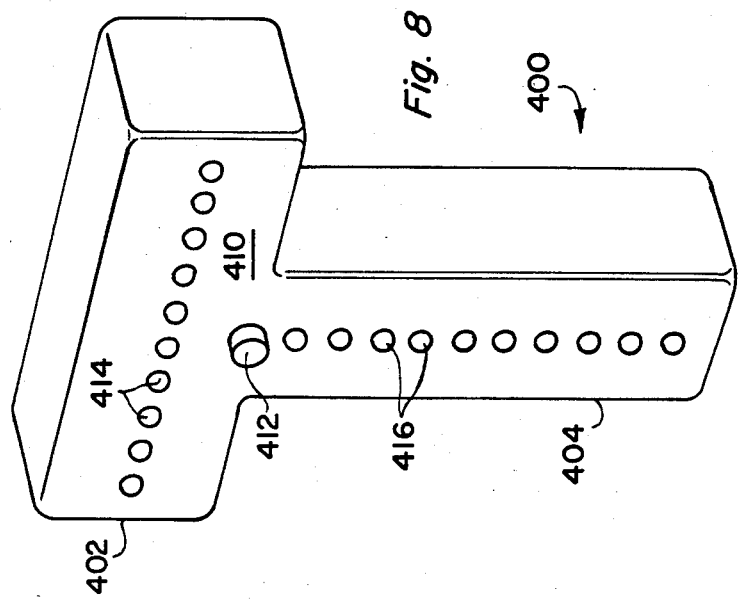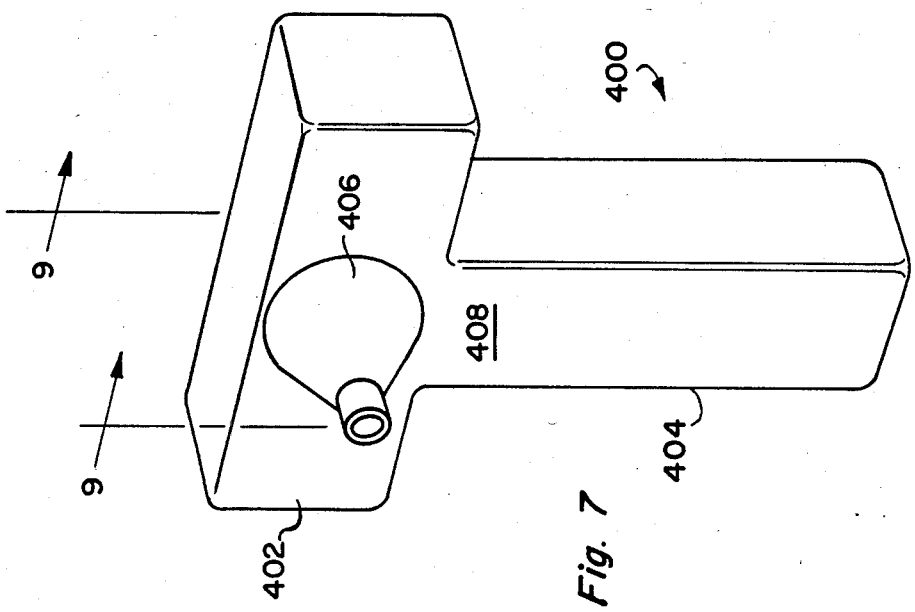

EAR PATHOLOGY DIAGNOSIS APPARATUS AND METHOD

This applicationn is a continuation-in-part of application Ser. No. 358,831, filed Mar. 16, 1982, now U.S. Pat. No. 4,459,966.

DESCRIPTION

1. Technical Field

The present invention relates generally to devices and methods for diagnosis of pathological ear conditions, and particularly to those devices and methods in which there are determined quantities related to the complex acoustic impedance of components of the ear.

2. Background Art

A wide variety of specific pathologic diseases associated with the human and animal ear have been identified. Among the more frequently identified pathologies are those comprising obstruction of the external canal, agenesis of the pinna, atresia of the external canal, perforation of the tympanic membrane, retraction of the tympanic membrane, otitis in its various forms (adhesive, purulent and non-purulent), otosclerosis, fixation of the stapes, and cholesteatoma, among others. In children, otitis media is one of the most common childhood pathologies. By itself, it is a significant affliction which can lead to serious long-term hearing and learning disabilities if not promptly diagnosed and treated. Further, it is frequently symptomatic of other pathologies, and thus useful in their diagnosis.

The diagnosis of otitis media in young children is particularly difficult because of the fear, or even pain, associated with the commonly available techniques of diagnosis. The usefulness of examination by conventional otoscopic techniques is often diminished by the discomfort of the child which leads, at best, to movement by the child which impairs the examination and, at worst, to a refusal to allow the examination to proceed. The problem is especially acute when the examination is to be made in the environment of a mass screening, such as may take place in hospital clinics where large numbers of patients must be seen in a comparatively short time. Similar problems are encountered in the useage of other diagnosis techniques, such as tympanometry.

Acoustic impedance measurements have also frequently been used to examine various characteristics of the ear in support of medical diagnosis. Prior-art acoustic impedance measurements of human ear structures are usefully summarized in the following patents:

| Patent | Inventor | Measurement Technique | Frequency In Hertz | Ear Canal Seal Required |
|---|---|---|---|---|
| 3,294,193 | Zwislocki | Impedance Bridge | 220 | Yes |
| 3,757,769 | Arguimbau | Measure Complex Y | 220 & 660 | Yes |
| 4,002,161 | Klar | Measure Compliance | 220 | Yes |
| 4,009,707 | Ward | Measure Compliance | 220 | Yes |
| 4,079,198 | Bennett | Impedance Bridge | Variable | Yes |

See also Pinto and Dallos, "An Acoustic Bridge for Measuring the Static and Dynamic Impedance of the Ear Drum", *IEEE Transactions on Bio-Medical Engineering*, Volume PME-15, No. 1, January 1968, Pages 10–16.

Typically, a probe such as that described in U.S. Pat. No. 4,057,051 (Kerovac), is inserted into the ear canal in such a way that the ear is effectively sealed from the external atmosphere. The probe is usually supplied with a means for varying the pressure within the ear canal above and below ambient pressure.

While the pressure is being varied, or at selected fixed values of pressure, a continuous wave (CW) sound signal, of constant amplitude, is introduced into the ear canal. The signal from the sound source, and the signal from the probe-mounted transducer, are variously combined to yield a measure of simple compliance (Klar, and Ward), impedance (Zwislocki, Bennett), or complex admittance (Arguimbau), at the entrance to the ear canal.

In most cases (Arguimbau, Klar, Ward), the measurement of acoustic admittance or compliance is direct, and made at a frequency of 220 or 660 Hz. In other cases (Bennett), impedance measurements are made in a bridge circuit, with an "Artificial Ear" as a reference, over a wider frequency range.

Commercially-available forms of the devices described in the above references include the Metz bridge, the Madsen Z0 70 electroacoustic impedance meter, and the Grason-Stadler model 1720 otoadmittance meter. In each of these devices, the external ear canal is sealed air tight and the pressure in it is varied from +200 mm of water to −400 mm while a selected characteristic of the eardrum is measured. In the Metz and Madsen devices, the selected measurement is the impedance (or compliance) of the eardrum at a single preselected frequency. In the Grason-Stadler device, the selected characteristic is the conductance (or susceptance) of the canal at two different frequencies, namely, 220 Hz and 660 Hz.

These approaches share many common characteristics: (1) measurements are made with low frequency CW audio signals, (2) an air-tight seal is required as a prerequisite for useful measurement, (3) any probe assembly must be inserted deep into the ear canal, (4) the air pressure in the ear canal must be varied above and below atmospheric for useful measurements, and (5) no continuous real-time display of diagnostic data is provided, (6) highly trained personnel are frequently required to conduct the test and to interpret the results, (7) the devices are frequently bulky, complex, and expensive, (8) patient cooperation is often a prerequisite to useful results. Commonly patients subjected to these diagnostic techniques may experience considerable discomfort. This is particularly the case with respect to young children (e.g., from a few months up to ten years old) who are apt to squirm and wiggle and thus make it more difficult to make the measurement and even, in some case, refuse to cooperate at all, particularly where prior experience with such measurements has resulted in significant discomfort.

DISCLOSURE OF INVENTION

In accordance with the present invention, I provide a simple, yet effective device (hereinafter denominated "reflection analyzer") and method for determining pathologic conditions of the ear. While the device and method of the present invention may advantageously be used for determining a wide range of possible pathologies, they are particularly useful for diagnosing the presence or absence of otitis media in young children, since the device and method are extremely fast in operation, thereby eliminating artifacts caused by motion of the child during testing; do not require pressurization of the ear canal, thereby eliminating a major source of the pain and fear associated with prior common measurement techniques; and do not require air tight physical contact between the measurement device and the ear of the patient being tested, or deep penetration into the ear canal, thereby further minimizing fear and eliminating pain otherwise associated with testing.

The present invention provides a unique method and apparatus that is particularly useful for diagnosis of effusions of the middle ear associated with otitis media. The method is practiced by determining a quantity related to the complex acoustic impedance of the middle ear, namely, the vector sum of an incident signal impinging on a microphone and thereafter propagating down the ear canal (treated as a lossy transmission line), and the same signal reflected back to the microphone from the ear, particularly from the tympanic membrane (ear drum) and middle ear components.

The results of such determination, made, in a preferred embodiment, over a wide band of audio frequencies (typically 1 KHz to 15 KHz), are examined to determine whether there is present a pathological dip in this vector sum, of a characteristic shape, and typically in a characteristic frequency region having a center lying between approximately 1.5 KHz and 5.5 KHz, depending on the age of the patient, the length of the probe, and on the ear pathology involved.

The method may be practiced with the apparatus of the present invention, which, in a preferred embodiment, comprises a reflection analyzer including a test head having a sound cavity, a transducer placed so as to create a sound field in the cavity, a hollow probe for conveying sound from the cavity to the vicinity of the ear canal, and for impedance matching to the ear canal, and a microphone suitably placed at the junction of the cavity and the probe. The analyzer also has a signal generator connected to the transducer, and appropriate arrangements for processing the signal from the microphone.

In a preferred embodiment, the analyzer provides a pulsed or continuous wave signal, that, over a suitable interval of time, varies in frequency and amplitude. With the apparatus so described, the method may be practiced with the ear at atmospheric pressure, and at least partially open to air in the atmosphere, thus making the invention particularly useful in the diagnosis of middle ear disease in young children and infants where insertion of probes and sealing the ear canal is either not desirable or not feasible. Specifically, the requisite measurements may be made with the measuring instrument of the present invention lightly touching the ear being examined but not necessarily forming an air tight seal with the ear. Thus, the pressure of the device against the ear is minimal and one source of possible pain essentially eliminated. Further, the measurement is typically made in a very short period of time, e.g., as little as twenty milliseconds (20 ms) or even less. Thus, the possibility of patient movement during the measurement sufficient to significantly interfere with the measurement is also essentially eliminated. Accordingly, the measurement is extremely fast, relatively accurate, non-invasive, and free of the pain commonly associated with such measurements. Thus, it is of significant utility in all kinds of diagnostic situations with respect to ear pathology, but particularly in those involving mass screening of the ears of young children for common pathologies such as Otitis Media.

The utility of the apparatus of the present invention is further enhanced in a second physical embodiment of the analyzer which takes the form of a "tee" held in a hand of the operator. A number of indicating devices, such as light emitting diodes (LED's), are positioned lengthwise along the horizontal arm of the tee, as well as vertically along the vertical leg of the tee, on a face of the device which is turned toward the user. The sound-emitting portion is positioned on the opposite face of the device, toward the patient being examined. The horizontally-oriented diodes indicate the frequency at which the selected indicating phenomenon (here, the dip in the vector sum) occurs, while the vertically oriented diodes indicate the magnitude of the dip in decibels. Thus, the diagnostic data is quickly and conveniently presented to the clinician in a clear and unambiguous form which is particularly useful in mass screening situations.

Accordingly, it is an object of the invention to provide an improved method and device for measuring ear pathologies.

Further, it is an object of the invention to provide a method and device for measuring ear pathologies which is particularly convenient to use.

Another object of the invention is to provide a device for measuring ear pathologies which performs the measurement rapidly and which quickly displays the result in a form convenient to the user.

Yet another object of the invention is to provide a device for measuring ear pathologies that is particularly suited for measuring ear pathologies of young children.

Still a further object of the invention is to provide a device for measuring ear pathologies which is well suited for mass-screening applications.

BRIEF DESCRIPTION OF THE DRAWINGS

FIGS. 7 and 8 are front and rear perspective views, respectively, of a further physical embodiment of a reflection analyzer in accordance with the present invention;

DESCRIPTION OF SPECIFIC EMBODIMENTS

Figure 1:
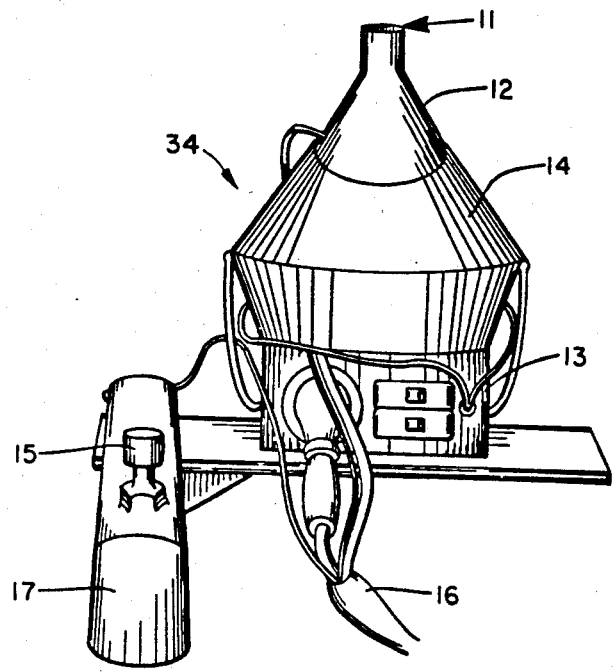
FIG. 1 shows a perspective view of a first physical embodiment of a test head in accordance with the present invention.

FIG. 1 is a perspective view of a test head 34 in accordance with a preferred embodiment of the present invention.

The microphone preamplifier 13a, is shown mounted on the rear of the transducer assembly 13. A microphone (shown in later figure) is mounted inside the hollow probe assembly 12. The diameter of the probe assembly is adjusted by changing the probe extension 11. The probe assembly 12 includes funnel-shaped section 12 in communication with sound cavity housing 14. The toggle switch 15 on handle 17 controls a recorder for capturing the output of the instrument. One of the cables 16 is shielded and carries signals from the probe-mounted preamplifier, while the other cable carries recorder control signals.

Figure 2:
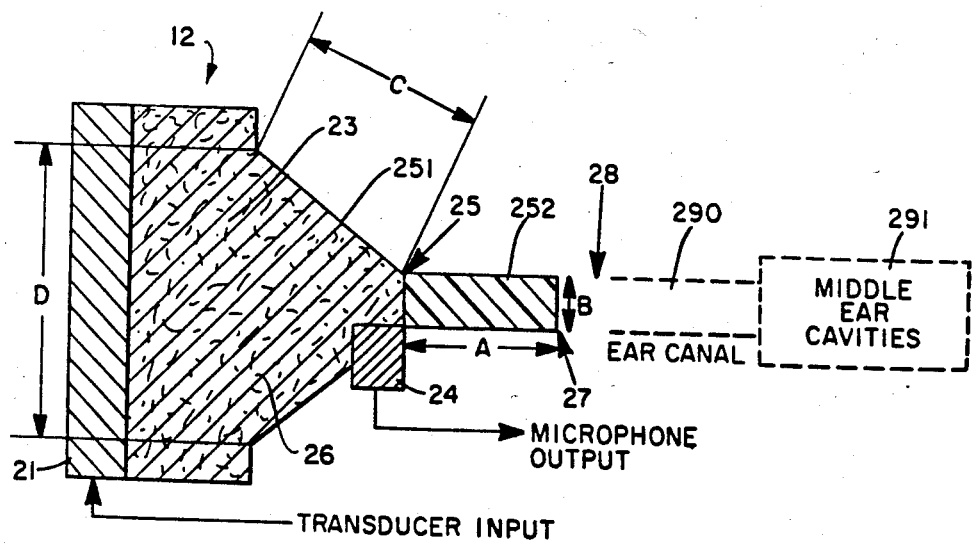
FIG. 2 shows a cross-section of the test head illustrated in FIG. 1.

FIG. 2 shows in cross section a view of the test head in FIG. 1. The test head includes a transducer 21 that creates a sound field in sound cavity 23. Sound in the cavity 23 is channeled through probe 25 to the vicinity of the ear canal 290. The probe has a funnel-shaped section 251 and two-piece linear section 252. Section 252 is choosen to match the dimensions of the typical healthy ear canal under test. This thereby matches the impedance of the probe tip and the typical ear canal. For children's ears, I have found that generally excellent results are obtained with length A of the linear portion 252 of the probe equal to approximately 1 cm and inner diameter B of the same section in the range of approximately, 0.25 to 0.75 cm. Similarly, good results are obtained when length C along the side of portion 251 of the probe is about 5 cm and the appoximate outer diameter D of the large end of the probe which is in contact with the sound cavity wall, is approximately 7 cm.

Although in some instances it may be desirable to substitute a probe extension with continuously variable inner diameter to match more exactly the input impedance of the ear canal under test, I have not found this to be mandatory for useful results. Good results have been obtained with a series of three probe extensions to match generally the ear canal impedances of infants children, and adults.

The operating principles of the invention are such that the probe extension need not be inserted into the ear canal. In practice there may be a narrow gap 28 between the test head probe tip 27 and the entrance to the ear canal 290. Control of this gap may be facilitated by a sponge rubber spacer attached at the end of probe tip 27.

The incident sound wave created by transducer 21 in the test head emanates from the test head at the tip 27 of the probe 25 and enters the ear canal 290. Thereafter, a portion of the incident wave is reflected by structures of the ear, including the tympanic membrane, stapes, and other components of the middle ear. The amplitude and phase of the reflected sound wave are a function of the test frequency used and the complex acoustic impedance of the ear canal and middle ear. In a healthy ear, one expects some minimal reflection from the tympanic membrane and middle ear. This can be suppressed by suitable selection of the inner probe tip diameter, e.g. by enlarging it to 1.0 cm for children. The complex acoustic impedance of the middle ear, in turn, depends very strongly on the conditions within the middle ear, and in particular on whether there is effusion present within the middle ear.

A portion of the reflected wave enters at tip 27 into the hollow probe 252 of the test head. The microphone 24 is located within the test probe 25 at the junction of the straight section 252 and the conical section 251. As a result, the microphone 24 measures the net sound pressure at this point; this net sound pressure is the vector sum of the incident and reflected signals. In order to reduce internal sound reflection and resonances within the test head, the sound cavity 23 is filled with loosely packed glass fibers. Good results have been obtained when the transducer 21 is one side of an electrostatic head phone, such as Koss ESP/10. In this preferred embodiment, the microphone is a condenser microphone.

Figure 3:
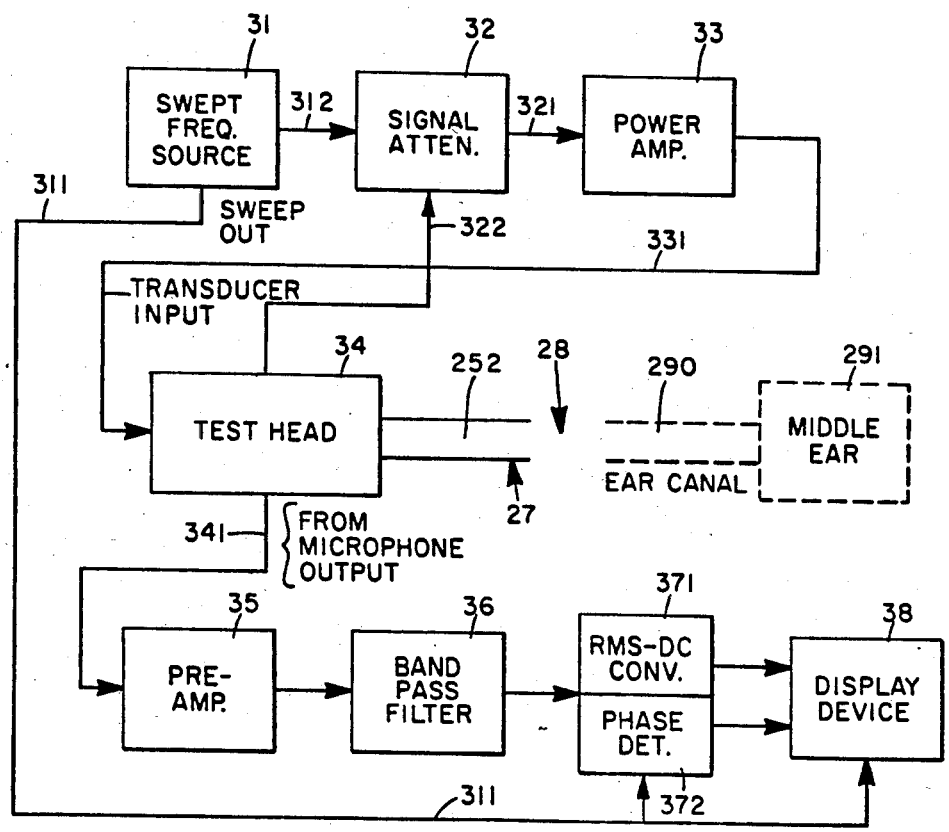
FIG. 3 presents a block diagram of an analog apparatus in accordance with the invention which utilizes a continuous sweep system.

FIG. 3 illustrates in a block diagram an embodiment of the apparatus of the invention utilizing all analog techniques with a continous sweep system. A sweep generator 31 provides a swept frequency output over line 312. Typically, the sweep may be from 1 kHz through about 15 kHz. A typical period for a full sweep may range from 20 milliseconds to about 10 seconds. These are, however, only typical figures. All that is necessary is that there be a frequency output that covers one or more of the resonant points of the ear canal "transmission line" as "terminated" by the middle ear. These points occur regularly at multiples of one quarter wavelength. The following resonant points have been found to be particularly useful for diagnostic purposes: ¼ wave, ½ wave, ¾ wave, and one wavelength. In normal adult ear these wavelengths correspond to frequencies of approximately 3.5, 7, 10.5, and 14 KHz.

The sweep signal itself appears as an output over line 311 for use in synchronizing the display device 39. The sound pressure from the transducer is kept at a constant level by feedback over line 322 to the attenuator 32. The voltage-controlled attenuator in this embodiment is continously adjustable to a maximum of 20 dB.

The output from the microphone 24 shown in FIG. 2 is sent over line 341 from the test head 34 through a preamplifier 35 to a bandpass filter 36. The bandpass filter typically passes signals from approximately 500 kHz to 20 kHz. The output of the bandpass filter 36 goes into both an RMS to DC converter 371 and a phase detector 372, so as to provide information as to both amplitude and phase of the signal in the microphone, which, as discussed in connection with FIG. 2, is the vector sum of the incident and reflected signals. The outputs of these devices 371 and 372 are then fed to an appropriate display device. Where the device is an oscilloscope, a high sweep rate, typically 50 Hz, can provide a flicker-free display. When the display device is a chart recorder, the sweep rate is typically 1 second or longer.

Figure 4:
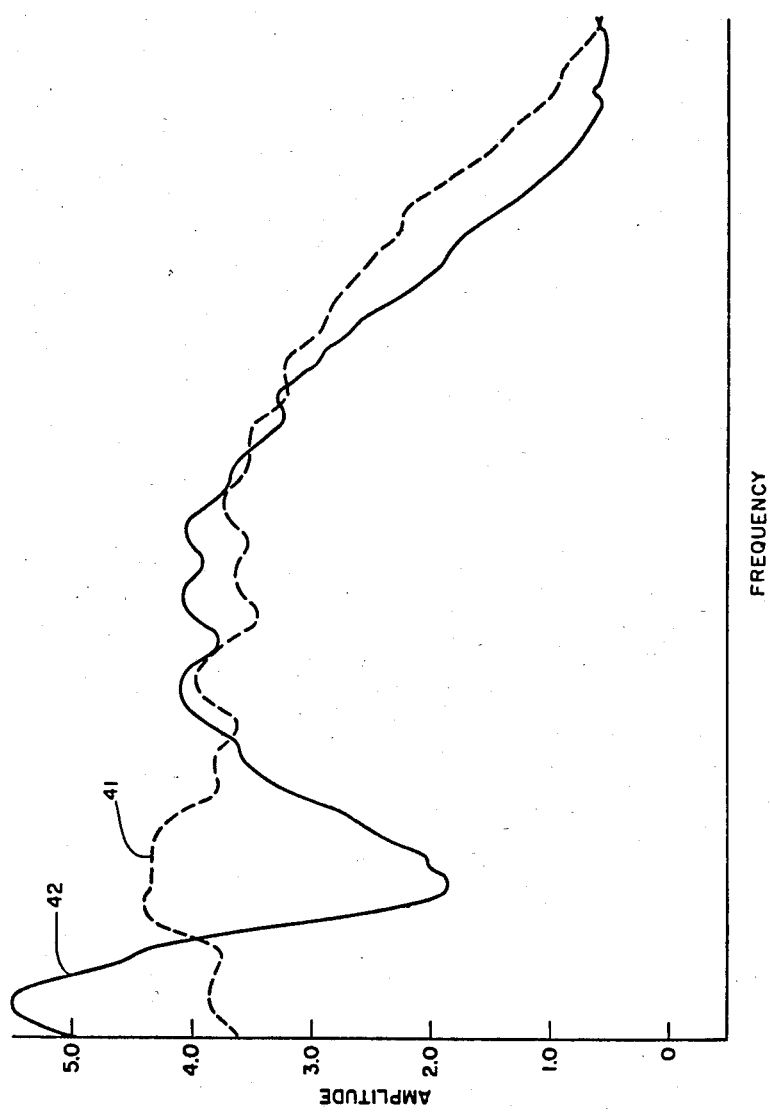
FIG. 4 presents a graph of measurements of the vector sum in a typical normal ear and the same quantity in an ear having a middle ear effusion.

FIG. 4 shows a typical graph produced when the embodiment shown in FIG. 3 is used in testing for middle ear effusion and otitis media. Curve 41 is a typical response curve for a nearly normal ear of a five year old child, while curve 42 is a typical curve for this same child with a pronounced middle ear effusion. I have discovered that the presence of effusion causes a pronounced dip in the magnitude of the vector sum at a frequency associated with quarter wave resonance (about 3.5 kHz in an adult) and have confirmed the theoretical validity of the dip as a diagnostic tool by computer analysis and modeling.

Figure 5:
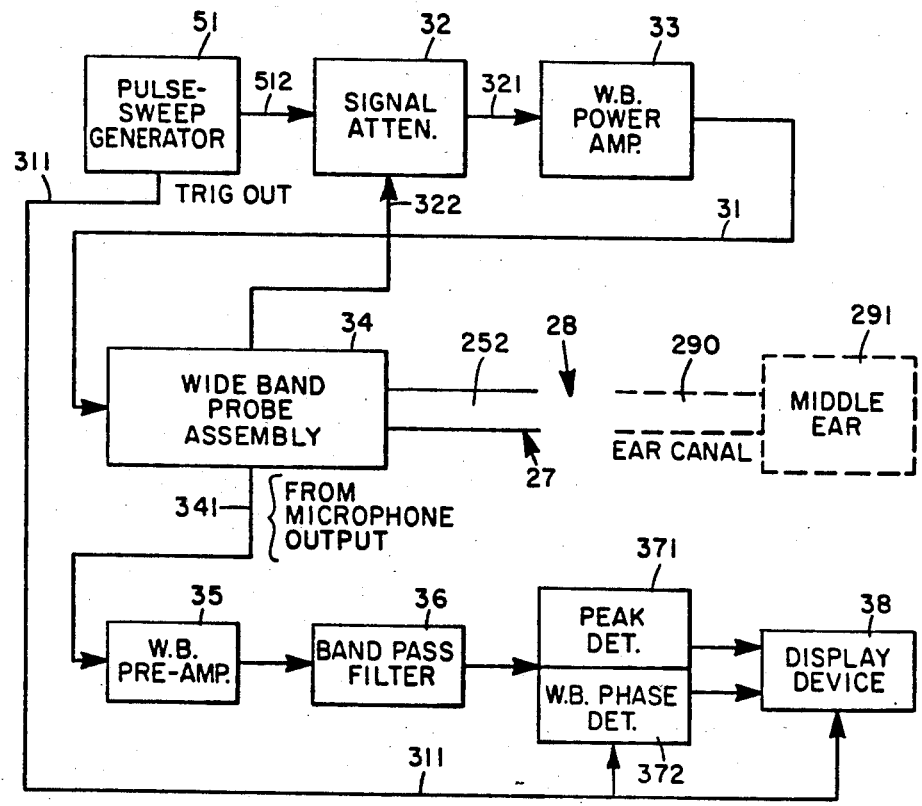
FIG. 5 presents a block diagram of an apparatus in accordance with the present invention utilizing a train of short audio pulses incremented in successive frequency steps.

FIG. 5 shows another embodiment of the apparatus of the present invention. In this embodiment, a train of pulsed signals is used, each pulse at a different frequency. Components bearing numbers corresponding to those numbers discussed in connection with FIG. 3 function in a manner analogously to their correspondingly numbered components in FIG. 3. In the embodiment shown in FIG. 5, however, the signal to the test head 34 originates with the pulse-sweep generator 51. The generator provides a series of pulses, each of which had a width of approximately 10 milliseconds, with a pulse repetition rate of approximately 100 Hz. Each has a different center frequency, the first pulse having a frequency of approximately 1 kHz. Each succeeding pulse has a center frequency approximately 120 Hz higher than its predecessor pulse, until the final pulse in a given train of pulses has a frequency of approximately 7 kHz. A complete diagnostic measurement can be made with a 0.5 second long burst of 50 pulses.

Figure 6:
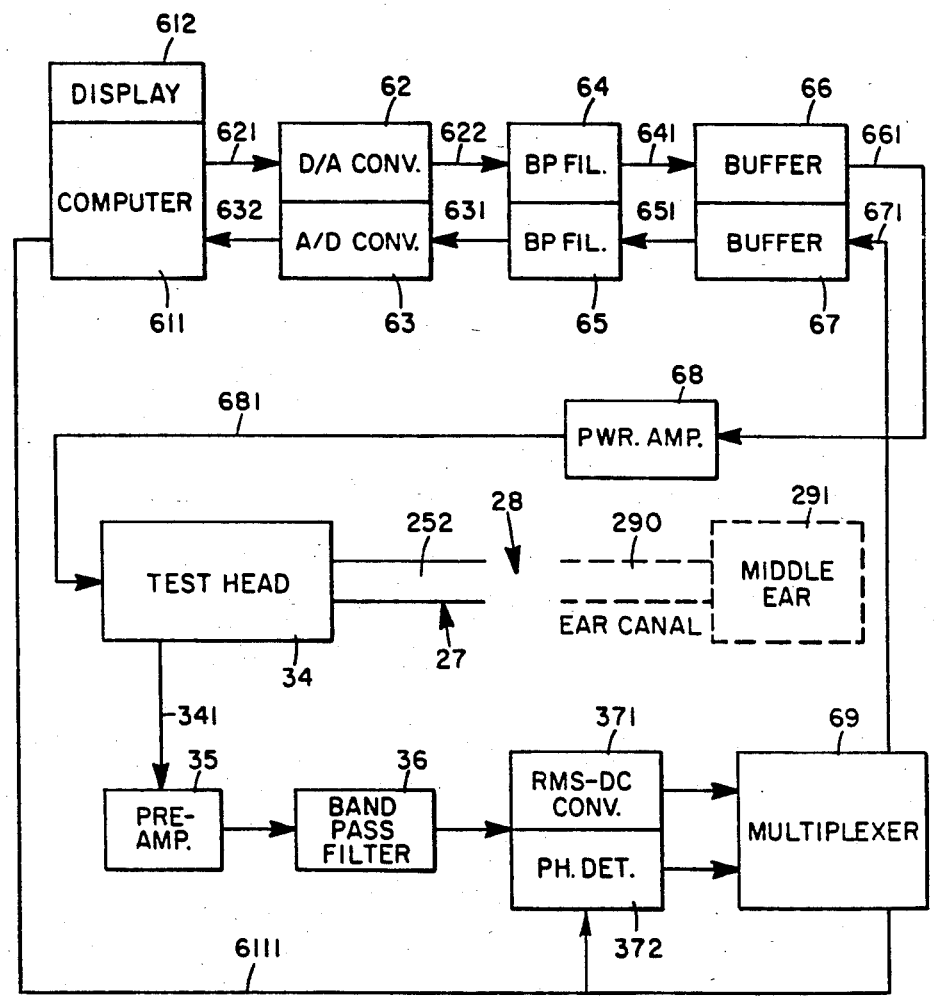
FIG. 6 shows a block diagram of a digitalized version of an embodiment of the invention utilizing a discrete sweep system.

A digital version of the apparatus employing discrete frequency jumps in a CW signal is illustrated in block diagram in FIG. 6. The processing of the signal from the microphone output of the line 341 is similar to the processing shown in connection with FIGS. 3 and 5. The principal difference is in the method of generating the signal going to the transducer in the test head 34. The signals are generated in a microprocessor-based computer 611. The computer's input and output are over lines 632 and 621 respectively from analog-to-digital converter 63 and digital-to-analog converter 62, respectively. Similarly, the converters 62 and 63 are each preceded (in the case of A/D converter 63) or followed (in the case of D/A converter 62) by an anti-aliasing bandpass filter 65-64 and buffer amplifiers 67-66. Buffer amplifier 67 receives over line 671 the output from the multiplexer 69, which in turn receives the information from the RMS-to-DC converter 371 and phase detector 372, which were discussed in connection with FIG. 3.

In this fashion, the processed microphone output (vector sum signal) passes through multiplexer 69, buffer amplifier 67, anti-aliasing bandpass filter 65, and analog-to-digital converter 63, to the microprocessor 611 so that additional signal processing can be performed to enhance the diagnostic value of the basic vector sum signal.

The microprocessor generates the swept signals that go to the transducer over line 681 via power amplifier 68. The signal waveforms are stored in tables in computer memory containing time-sampled waveforms, so that the signals are generated digitially for every frequency sweep. Entries in the tables are scanned at user-defined rates, to produce the stepped frequency sweeps. In this fashion, there can be controlled many different parameters, such as starting frequency, stopping frequency, frequency step size, frequency linearity, etc. This same technique provides precise control over the amplitude of the signal at each frequency step, so as to compensate for (for instance) signal channel gain variations between the output of digital-to-analog converter 62 and the transducer in the test probe discussed with reference to FIG. 2. Further, with respect to signal generation, use of the approach shown in FIG. 5 permits user control over signal type (e.g., pulse or CW), signal amplitude, and signal phase, whether the signal includes a burst of pulses as the device in connection with FIG. 5 or a continous analog generated sweep, as in FIG. 3. Furthermore, processing of the collected data can also be achieved readily. Quantitative results can be displayed, or the computer can be asked to detect the presence, frequency center line, shape and depth of the characteristic dip described previously, and give a single "go"—"no go" i.e., effusion—no effusion) response to the user.

Figure 9:
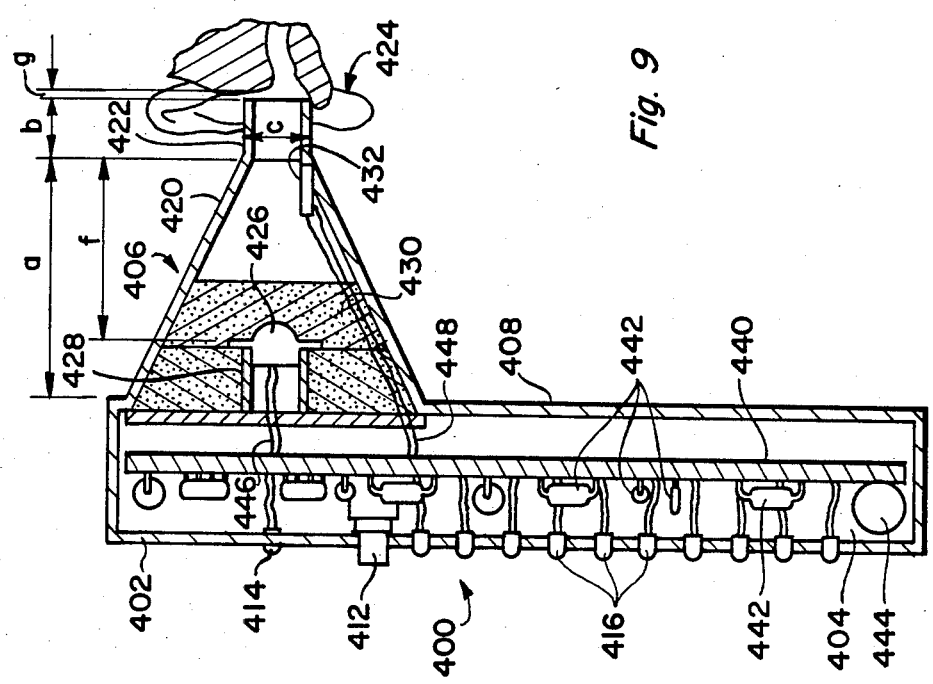
FIG. 9 is a vertical sectional view of the analyzer along the lines 9—9 of FIGS. 7 and 8.

Turning now to FIGS. 7 through 9, an alternative physical embodiment of the reflection analyzer of the present invention is shown in detail. The analyzer of FIGS. 7 through 9 is completely self-contained; is small enough to be held in the user's hand, and is thus readily portable; and provides a particularly convenient output display for quickly informing the user-clinician of the condition of the ear being examined. The analyzer of this embodiment comprises a hand-held casing 400 in the form of a "tee" having a horizontal upper arm 402 and a vertically-extending lower arm 404. A probe assembly 406, corresponding to the probe assembly 12 of FIGS. 1 and 2, is mounted on a front face 408 of the probe. A back face 410 of the probe (FIG. 8) carries a switch 412, a horizontal row of light-emitting diodes 414 and a vertical row of light emitting diodes 416.

The diodes 414 indicate the frequency at which the resonance dip occurs, while the diodes 416 indicate the amplitude of the dip. For purposes of illustration, a sequence of ten diodes has been shown in the horizontal row 414 and, thus, the range of zero to 7500 Hz can be covered by energizing the diodes at frequencies which are spaced 750 Hz apart from each other. Frequencies in between the frequencies precisely corresponding to any pair of diodes may be indicated by energizing two diodes simultaneously and proportionally to the closeness of the corresponding frequency of the respective diodes so that the amplitude of light emitted by the respective diodes is an indication of how close the resonance (dip) frequency is to the respective diodes. A skilled clinician is rapidly able to interpolate the actual frequency from this information with surprisingly good accuracy.

The probe assembly 406 is shown in greater detail in FIG. 9 which is a cross-sectional view along the lines 9—9 of FIG. 7. The assembly comprises a conical shell 420 extending from the front face 408 of the analyzer and terminating in a tip 422 through which the acoustic waves pass into an ear 424 adjacent to which the analyzer is positioned. As was the case with the probe assembly 12 of FIG. 2, the interior of the shell 420 is hollow and contains a first acoustic transducer in the form of a miniature loudspeaker 426 mounted in a conical shell 428 and surrounded by sound-absorbing material 430 such as an open cell polyurethane foam. The foam introduces acoustic resistance within the conical shell 420 which serves to minimize undesired acoustic reflections and resonances within the shell; additionally, it broadens the measured resonance.

Positioned towards the front of the shell 420, but behind the rear of the tip 422, is a second acoustic transducer 432 comprising a microphone. The microphone 432 is preferably disposed with its input surface oriented in a horizontal plane aligned with the bottom of the tip opening and immediately adjacent the tip opening (as seen in FIG. 9), this point is selected to minimize undesired reflections. The microphone measures the sound pressure level at its surface which, as was the case with the microphone 24 of FIG. 2, is the vector sum of the pressure generated by speaker 426 and the pressure generated by the back reflections from ear 424. As was the case with the embodiment of FIGS. 1 and 2, and as shown in detail in FIG. 4, the net sound pressure at the microphone 432 will exhibit a pronounced dip at around 3500–4000 Hz in the prsence of otitis media as the applied sound wave is swept over a frequency from a low value (e.g., a few hundred hertz) to a higher value (e.g., 5 to 7 kHz). In contrast, a healthy ear will exhibit no such sharp dip and thus a diagnosis of a pathologic condition is readily made.

The entire electronics for generating and processing the acoustic signals is contained within the shell 400. In particular, a printed circuit board 440 carries the typical components 442 such as capacitors, resistors, integrated circuits, diodes, etc. as well as one or more batteries 444 which provide power for the operation of the unit. Leads 446 and 448 connect the speaker 426 and the microphone 432, respectively, to the circuit board.

As noted previously in connection with the probe assembly 12 of FIGS. 1 and 2, the analyzer 400 of FIGS. 7 through 9 detects resonances occurring at $\frac{1}{4}$, $\frac{1}{2}$, $\frac{3}{4}$ and 1 wavelengths, respectively. Consistent with this mode of operation, a physical embodiment of the analyzer of FIGS. 7 through 9 has been constructed with a cone length "f" equal to about 7.3 cmm to thereby position the microphone at a mode for unwanted reflections at three-quarter wavelength; a tip length "b" equal to 1 cm; a tip inner diameter "c" equal to 0.5 cm (for neonates; for children and adults the appropriate diameters are 1 and 2 cm, respectively). Control of the position of the microphone 432 with respect to the speaker 426 and the tip 422 in this manner can significantly contribute to the uniformity of response across a range of frequencies.

The inner diameter "c" of the tip determines the impedance matching between the analyzer and the ear 424. Effectively, it acts as an impedance transformer between the two and, by proper proportioning of the inner diameter, allows one to remove the analyzer 400 from direct contact with the ear 424 and separate them by a small gap g which may be 1 millimeter or so. This leads to several significant benefits. To begin with, the fact that the instrument need not have an air-tight seal to the ear significantly reduces the fear of the patient, particularly children, and encourages their cooperation in the measurement. This is in marked contrast to prior instruments which may clamp extensive apparatus around the patient's head and pressurize the ear canal. Further, decoupling the analyzer from the need for exact positioning with respect to the ear allows rapid but accurate analysis of ear pathologies, a characteristic which is particularly important in mass screening situations such as in the clinics of large urban hospitals.

The tip 422 may be proportioned to the ear canal diameters of the population being examined (e.g., neonates, children, adults) or may be selected to be such that it can accomodate measurements on one element of the population (e.g., adults) with a minimum, yet acceptable, sensitivity, and will thus accomodate measurements on the other elements of the population with higher sensitivity. For example, the diameter of the outer ear canal of neonates is of the order of 2.0 mm; that of children is of the order of 4 mm; and that of adults is of the order of 8 mm. By utilizing a tip having compromise inner 100 mm, one provides at least a limited degree of decoupling between the analyzer and the ear with respect to adults; a somewhat greater degree of decoupling with respect children; and the maximum degree of decoupling with respect to infants. Thus, the decoupling is the most for those patients who can be expected to be the most cooperative and the least for those who are likely to be the least cooperative, which is precisely what is desired.

It should be noted that as the ratio of tip diameter to ear canal diameter increases, the resonance dip becomes more shallow; broadens to a certain extent; and may shift in frequency. Thus, it is desirable to balance the desire for maximum decoupling (which calls for large ratios of tip diameter to ear canal diameter) with the desire for maximum differentiation between (which calls for smaller ratios of tip diameter to ear canal diameter). My invention allows the designer to establish the desired balance conveniently and inexpensively. Further, by providing the clincian with a variety of tips which can be fitted to the conical shell 406 (e.g., by snap-fit, threaded fit, or other well known attaching means), the clinician can himself select the tip most suited to the patient being examined. Where a single tip diameter only is to be provided, it is preferred that a tip diameter of from one to two times the diameter of the typical ear canal to be examined be used to thereby balance analyzer sensitivity in distinguishing healthy ears from diseased ears (smaller ratio indicated) against desired decoupling (larger ratio desired).

Figure 10:
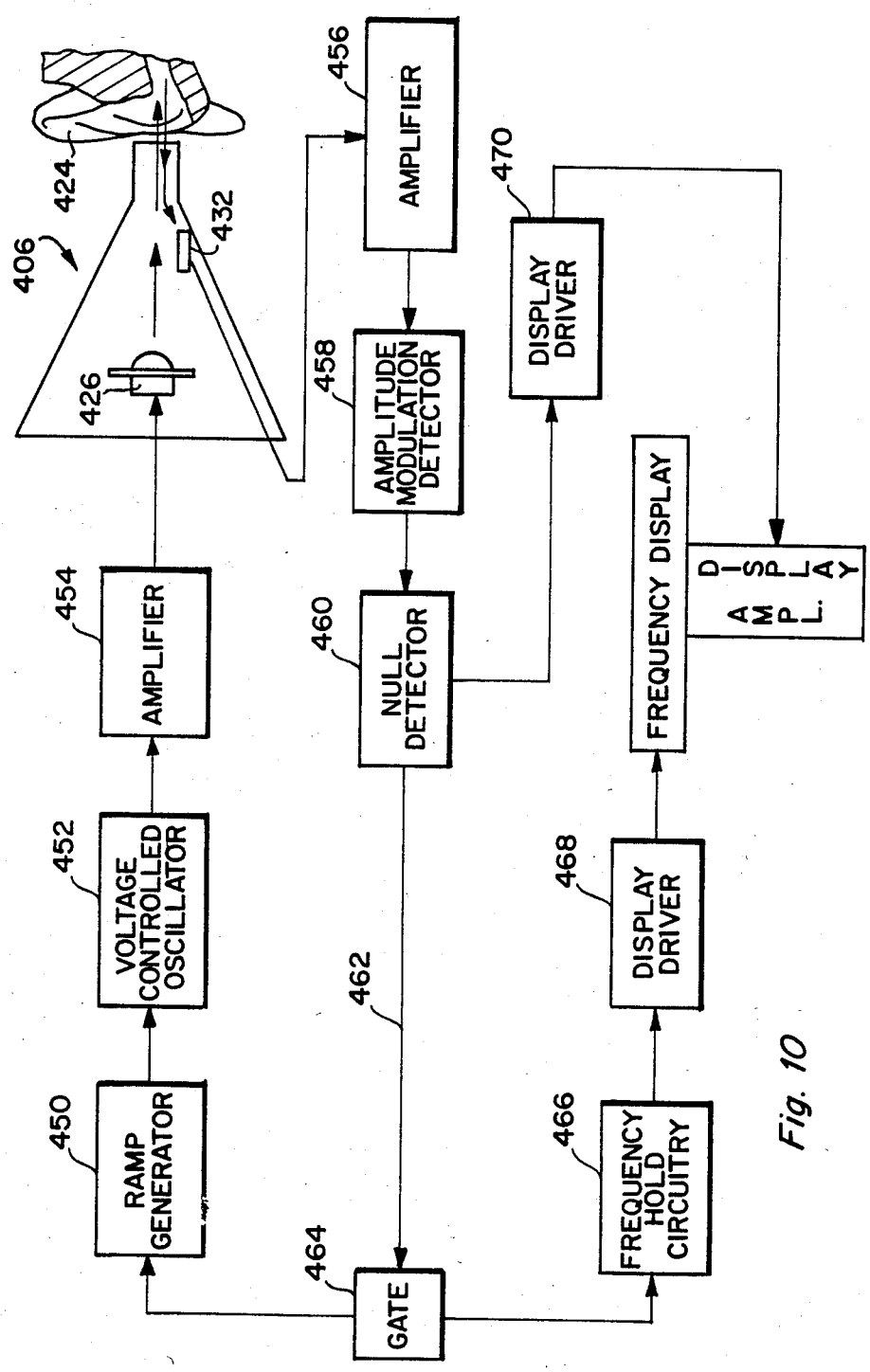
FIG. 10 is a block and line diagram of measurement circuitry for the analyzer of FIGS. 7-9.

FIG. 10 is a simplified block and line diagram of driving and measurement circuitry particularly suited to the analyzer of FIGS. 7-9. Generator 450 generates a rising ramp which drives a voltage controlled oscillator 452 to generate a sinusoidal wave output of continuously increasing frequency. Preferably, the frequency increases from a low frequency (e.g. approximately 150 Hz) to approximately 7 kHz in a time duration of on the order of 70 ms. The output of the oscillator 452 is applied to an amplifier 454 and thence to the speaker 426 in head 406. The acoustic waves generated by the speaker 426 are fed through the probe tip and into the ear 424. The reflected waves return through the tip of the probe 406 and impinge upon the microphone 432, together with the incident waves from speaker 426. The output of the microphone is fed to an amplifier 456 and thence to a detector 458 which follows and measures their amplitude.

A null detector 460 follows the output of amplitude detector 458 and stores the minimum amplitude of the particular measurement. The null is determined to be at that frequency at which the amplitude again begins rising (by more than a predetermined thereshold amount) after falling for at least a predetermined amount. The threshold levels are selected to provide acceptable sensitivity while masking noise and other artifacts in a manner known to those skilled in the art. The null detector provides a gating signal 462 to a gate 464 on detection of a null. Gate 464 couples the instantaneous output of the ramp generator 450, at the time of the gating signal 462, to frequency hold circuitry 466 which records the frequency corresponding to the occurrence of a minimum as marked by null detector circuit 460. An output signal corresponding to the null frequency is applied to the frequency display portion of the analyzer (which includes the frequency display diodes 414) via a display driver 468, while an output corresponding to an amplitude of the detected minimum is applied by null detector 460 to the amplitude display portion of the analyzer (which includes amplitude display diodes 416) via a display driver 470. The precise circuitry forming the elements shown in FIG. 10 forms no part of the present invention and need not be further described in detail. Further, a "pre-listen" control may advantageously be utilized to suppress the measurement during periods of high ambient environmental noise.

It will be understood by those skilled in the art that the resonance condition can also be determined from the large phase shift that accompanies the transition through resonance (dip). Thus, detection of this phase shift offers an important alternative approach to detecting the amplitude of the dip at the various resonant points.

CONCLUSION

From the foregoing, it will seen that I have provided a significantly improved device for diagnosing ear pathologies. The analyzer of the present invention is useful for a wide range of ear pathologies, and offers significant advantages with respect to ease of use, speed of use, and minimal physical contact with the patient, among other advantages. It is sufficiently sensitive as to detect significant ear pathologies, while passing normal or healthy ears. Further, it is largely immune to environmental noise or patient-induced artifact. It is particularly useful in connection with mass screening situations in which large numbers of examinations must be conducted in a comparatively short time, and frequently with patients unable or unwilling to provide any significant degree of cooperation. The analyzer is decoupled from air-tight physical contact with the subject being examined and thus the fear and discomfort frequently associated with instrumental examination of the ear are eliminated. Further, the measurement is made over a very short interval of time and thus the chance of patient movement interfering with the test is minimized.

While the invention has been described with particular reference to specific embodiments thereof, it will be understood that it may be embodied in a variety of forms diverse from those shown and described without departing from the spirit and scope of the invention as defined by the following claims.

I claim:

1. Apparatus for detecting pathologic ear conditions, comprising
   A. an acoustic signal generator providing an acoustic output that sweeps over a frequency range of at least several kilohertz during a measurement,
   B. an acoustic waveguide having an input end coupled to receive the output of said generator and an output end positionable adjacent to and exteriorly of the outer canal of an ear being examined and transmitting acoustic waves into the outer canal of said ear, said output end characterized by an acoustic output impedance that is less than the acoustic input impedance of a typical canal to be examined;
   C. a microphone positioned to receive inputs from both the generator and from reflections from said ear, and providing an output indicative of the sum of said inputs,
   D. means for displaying at least a portion of the output of said microphone for detecting departure of said output from the expected output for a normal ear.

2. Apparatus according to claim 1 in which said waveguide output end has an acoustic output impedance that is no greater than one-quarter the acoustic input impedance of said ear canal.

3. Apparatus according to claim 1 in which said waveguide, at the output end thereof, has a diameter no less than twice the diameter of said canal at the input thereof.

4. Apparatus according to claim 3 in which said generator provides an acoustic output that sweeps over a frequency of from at least 2 KHz to 7 KHz during a time interval not greater than one second.

5. Apparatus for detecting pathologic ear conditions, comprising
   A. means for applying to an ear canal to be examined an incident acoustic signal that ranges over a frequency of at least greater than a kilohertz
   B. means for comparing said incident signal with signals reflected back through said ear canal to detect the occurrence of a resonance condition, and
   C. means providing an indication of the frequency and amplitude of a detected resonance.

6. Apparatus according to claim 5 in which said indication means comprises a first linear visual indication means for providing direct visual indication of the frequency of a detected resonance and a second linear visual indication means for providing direct visual indication of the amplitude of a detected resonance.

7. Apparatus according to claim 6 in which said first visual indication means comprises a horizontally disposed row of light-emitting diodes and said second visual indication means comprises a vertically-disposed row of light-emitting diodes.

* * * * *